(12) United States Patent
Chen et al.

(10) Patent No.: US 8,172,123 B2
(45) Date of Patent: May 8, 2012

(54) SURGICAL STAPLING HEAD ASSEMBLY WITH A ROTARY CUTTER

(75) Inventors: Wangdong Chen, Jiangsu (CN); Wei Xu, Jiangsu (CN); Shouye Xie, Jiangsu (CN)

(73) Assignee: Suzhou Touchstone International Medical Science Co., Ltd., Jiangsu (CN)

( * ) Notice: Subject to any disclaimer, the term of this patent is extended or adjusted under 35 U.S.C. 154(b) by 288 days.

(21) Appl. No.: 12/666,964

(22) PCT Filed: Jun. 26, 2008

(86) PCT No.: PCT/CN2008/001226
§ 371 (c)(1),
(2), (4) Date: Dec. 28, 2009

(87) PCT Pub. No.: WO2009/000160
PCT Pub. Date: Dec. 31, 2008

(65) Prior Publication Data
US 2010/0187286 A1   Jul. 29, 2010

(30) Foreign Application Priority Data

Jun. 28, 2007 (CN) .......................... 2007 1 0024761
Sep. 7, 2007 (CN) .......................... 2007 1 0132025

(51) Int. Cl.
*A61B 17/068* (2006.01)
(52) U.S. Cl. ..................... 227/180.1; 227/19; 227/175.1; 227/179.1
(58) Field of Classification Search ............... 227/180.1, 227/19, 175.1, 179.1
See application file for complete search history.

(56) References Cited

U.S. PATENT DOCUMENTS

| | | | |
|---|---|---|---|
| 4,304,236 A * | 12/1981 | Conta et al. | 227/179.1 |
| 4,903,697 A * | 2/1990 | Resnick et al. | 227/178.1 |
| 7,588,176 B2 * | 9/2009 | Timm et al. | 227/179.1 |
| 2005/0187576 A1* | 8/2005 | Whitman et al. | 606/219 |
| 2005/0283191 A1* | 12/2005 | Fontayne et al. | 606/219 |

* cited by examiner

*Primary Examiner* — Brian D Nash
(74) *Attorney, Agent, or Firm* — Morris Manning & Martin LLP; Tim Tingkang Xia, Esq.

(57) ABSTRACT

A rotary cutter head for a surgical stapling instrument includes a staple cartridge, an annular cutter, a staple-pushing seat and a staple chamber. The staple-pushing seat and the annular cutter are connected by a bearing structure and provided with guide projections. The inner wall of the staple cartridge or the outboard of the expand-stopping tube is integral injection molded with a metal cylinder insert, on which is provided with a forward helix track and a backward track mutually independent and communicated with each other. The guide projections are mated with the two guide tracks and guiding the annular cutter to move along a helical path.

9 Claims, 2 Drawing Sheets

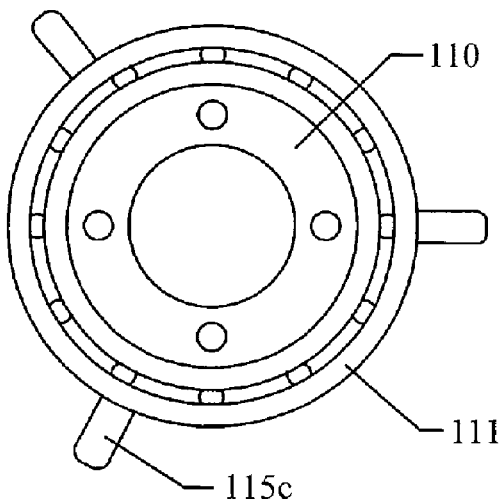
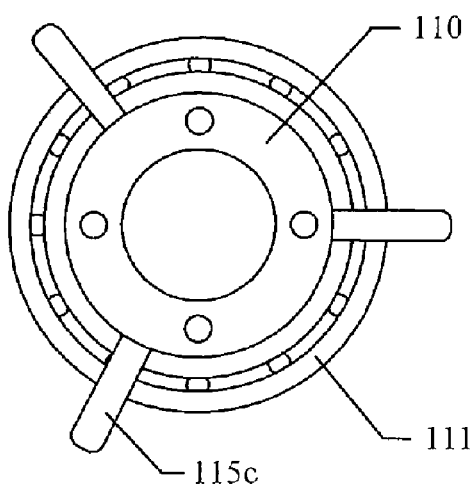
Fig. 6                                   Fig. 7
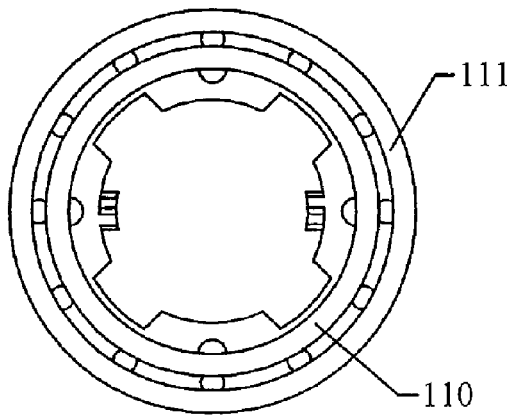
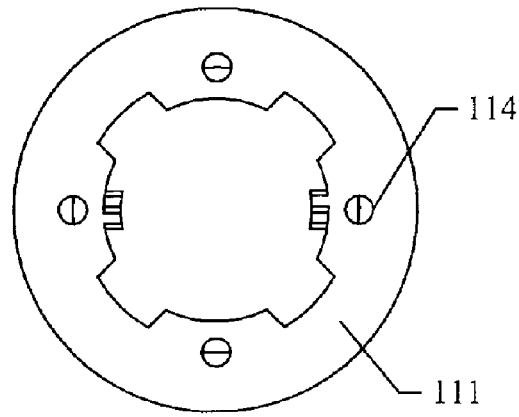
Fig. 8                                   Fig. 9

SURGICAL STAPLING HEAD ASSEMBLY WITH A ROTARY CUTTER

FIELD OF THE INVENTION

The present invention relates to a surgical stapling head assembly, more particularly, to a rotary cutter for surgical stapling head assembly in the technical field of medical instrument.

BACKGROUND OF THE INVENTION

A surgical stapling head assembly is the medical instrument used for performing a circular anastomosis stapling operation, which can be operated easily and the surgery operation time can be effectively reduced. The surgical stapling head assembly has distinct advantages over the manual suture, which is approved by more and more doctors and patients. A circular stapling instrument is used for performing a circular anastomosis stapling operation, unwanted tissues are cut while suturing, however, the annular cutter of prior art works in way of straight forward and straight backward thereby the doctor has to exert large force when doing the operation so that tissues are able to be cut by impulsive force, sometimes the tissues may not be cut completely and the uncut tissues will be stretched to break by the force from the stapling instrument while retreating, which brings tensile damages to anastomosis ring and the result is serious. To overcome the defects as mentioned above, rotary cutting instrument is invented by changing the straight cutting of prior art into rotary cutting, the cutting effects are greatly improved and the doctors can exert much less force when doing operations.

However, tracks for rotary cutting have comparatively monotonous function, the same helix tracks function not only as forward tracks but also function as backward tracks, the annular cutter has to rotate to retreat and it suffers comparatively large resistance because the backward journey is comparatively long. Furthermore, the rotary cutter of prior art is enabled by disposing ball device between the annular cutter and staple driver, the rotary cutter is connected with the staple driver by means of two slender catches, when the annular cutter is pressed tightly with the staple driver by the catches, the annular cutter will be subject to large friction resistance; when the annular cutter is pressed loosely with the staple driver by the catches, due to influences from self gravity and other factors, the annular cutter may deviate from central axis slightly when cutting tissues, therefore, the shape of the cut is not a full circle, there is a potential danger of cutter being stuck and unmovable when the annular cutter deviates too much from the central axis, which may affect the implementation of the surgery operations.

SUMMARY OF THE INVENTION

The invention is aimed at solving the problems of prior art by providing a surgical stapling head assembly with a rotary cutter.

The object of the present invention is achieved by the following technical scheme: a surgical stapling head assembly with a rotary cutter comprises a casing, an annular cutter, a staple driver and a staple holder, the casing is a tubular body comprising a stepped inner cavity and an anti-expansion tube, a plurality of staple pushers are arranged annularly and alternately in two rows, and are disposed between the anti-expansion tube and an inner wall of the casing, the staple driver is disposed at a proximal end of the staple pushers, the staple holder for receiving one or more surgical staples is disposed at a distal end of the staple driver, the annular cutter is disposed in the space formed by an inner wall of the staple holder, wherein said annular cutter is connected with the staple driver by a bearing structure, the bearing structure at least comprises a bearing inner ring and a bearing outer ring, guiding projections are disposed on said annular cutter or the bearing inner ring or the bearing outer ring, a metal cylinder member with guiding tracks is disposed inside the casing, said guiding projections engage with the guiding tracks so as to guide the annular cutter to move along a helical path.

Preferably, in the surgical stapling head assembly with a rotary cutter, said metal cylinder member is molded on an outer wall of the anti-expansion tube. or on the inner wall of the casing; corresponding to these two ways, said guiding projections can be disposed at the proper location of the annular cutter or the bearing inner ring or the bearing outer ring so as to engage with the guiding track of the metal cylinder member.

Preferably, in the surgical stapling head assembly with a rotary cutter, said guiding track comprises a helix forward track and a backward track, the helix forward track and the backward track are independent from each other but communicated with each other to form at least one back and forth journey. more preferably, said backward track comprises a section of straight line track and a section of arc track, the angle between the two edges of the straight line track and the axis of the metal cylinder member is from 0° to 30°.

Preferably, in the surgical stapling head assembly with a rotary cutter, said bearing structure comprises the bearing inner ring, the bearing outer ring and a transmission part, the bearing inner ring is connected with the bearing outer ring by the transmission part, the annular cutter is fixed on the bearing inner ring or the bearing outer ring; more preferably, bearing inner ring and said annular cutter can be fixed by rivets through the rivets holes thereof; or bearing outer ring and the annular cutter can be fixed by rivets through the rivets holes thereof.

The present invention has following advantages: by employing bearing structure, the annular cutter can be connected tight with the staple driver by mechanical structure, the annular cutter will not deviate from the central axis when the annular cutter moves along a helical path, the section of tissues cut in surgery operations are in shape of full circle so as to avoid the potential danger of the cutter being stuck and unmovable, the surgery operations is ensured successful. Moreover, during the operation process, the annular cutter rotatingly forwards along the helix track when going forward, and backwards to the inner cavity of the staple holder in way of straight line or part of straight line under the guide from the backward track, the operation of forwarding and retreating which is previously realized by one helix track is divided into two parts, the helix track undertakes the forward operation and the backward track undertakes the backward operation, the forward helix track is communicated with the backward track to form at least one back and forth journey, which shortens the backward journey and reduces the resistance subjected by the annular cutter when retreating, the time consumed for retreating is reduced as well, therefore, the surgery operations can be implemented more easily with more safety.

BRIEF DESCRIPTION OF THE DRAWINGS

The objects, features and advantages of the present invention will become apparent from the following detailed description of the preferred embodiments, with references to the appended drawings, which are intended for illustrative but not limitative purposes. While the embodiments are provided as typical technical solutions of the present invention, various modifications, alternative constructions and equivalents may be employed without departing from the true spirit and scope of the present invention.

FIG. 6 is a schematic view of another bearing structure of the present invention;

FIG. 7 is a schematic view of the third bearing structure of the present invention;

FIG. 8 is a front view of the bearing structure of the present invention;

FIG. 9 is a bottom view of the bearing structure of the present invention. in which:

| No. | Denotes | No. | Denotes |
| --- | --- | --- | --- |
| 101 | casing | 102 | staple driver |
| 103 | annular cutter | 104 | anti-expansion tube |
| 105 | metal cylinder member | 106 | forward helix track |
| 107 | straight line backward track | 108 | arc backward track |
| 109 | bearing structure | 110 | bearing inner ring |
| 111 | bearing outer ring | 112 | ball |
| 113 | washer | 114 | rivet hole |
| 115a | guiding projection | 115b | guiding projection |
| 115c | guiding projection | | |

DETAILED DESCRIPTION OF THE PREFERRED EMBODIMENTS

First Embodiment

A surgical stapling head assembly with a rotary cutter as illustrated from FIGS. 1 to 5 comprises a casing 101, a staple driver 102, an annular cutter 103 and a staple holder, the casing 101 is a tubular body with a stepped inner cavity and an anti-expansion tube 104 is disposed therein, a plurality of staple pushers are arranged annularly and alternately in two rows, and are disposed between the anti-expansion tube 104 and the inner wall of the casing 101, the staple driver 102 is disposed at the proximal end of the staple pushers, the staple holder is disposed at the distal end of the staple pushers, the annular cutter 103 is disposed in the space formed by the inner wall of the staple holder.

Figure 2:
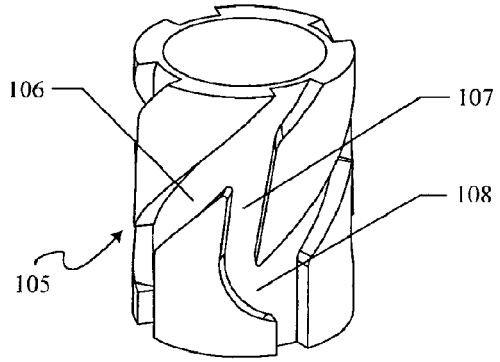
FIG. 2 is a schematic view showing the structure of the metal cylinder member of the present invention.
Figure 4:
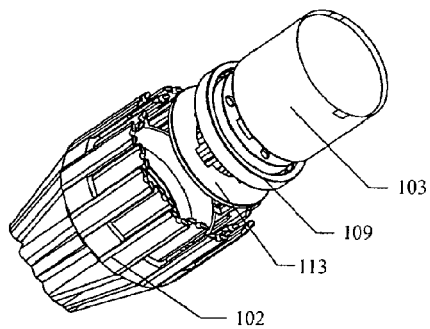
FIG. 4 is a schematic view showing the partial assembly of the present invention.
Figure 5:
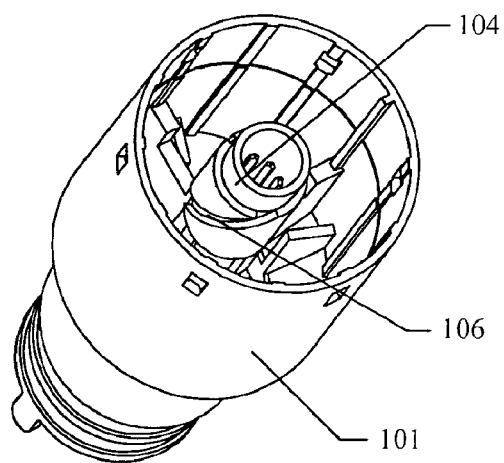
FIG. 5 is a schematic view showing the structure of the casing of the present invention.

A metal cylinder member 105 is molded on the outer wall of the anti-expansion tube 104, of which the structure is illustrated in FIG. 2, a forward helix track 106 and a backward track are distributed on the outer wall of the metal cylinder member 105, a guiding structure is disposed on the annular cutter 103 and the guiding structure is inserted via the entrance of the forward helix track 106 so that the annular cutter 103 is rotatably connected with the metal cylinder member 105, the bottom of the annular cutter 103 is fixed on the staple driver 102 by the bearing structure 109, a washer 113 is disposed between the bearing structure 109 and the staple driver 102 as illustrated in FIG. 4.

Figure 1:
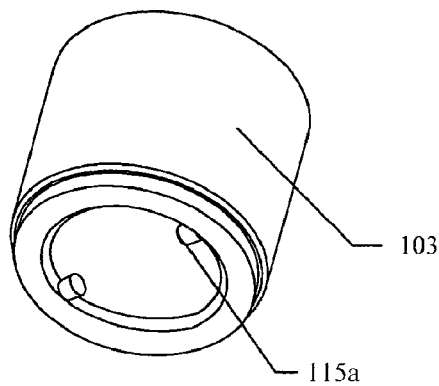
FIG. 1 is a schematic view showing the structure of the annular cutter of the present invention.

Furthermore, said guiding structure is in the form of guiding projections 115a, guiding projections 115a are disposed on the inner wall of the bottom of the annular cutter 103 as illustrated in FIG. 1. At the same time, said forward helix track 106 is communicated with the backward track to form at least one back and forth journey, and the backward track comprises a section of straight line track 107 and a section of arc track 108, the angle between the two edges of the straight line backward track 107 and the axis of the metal cylinder member 105 is from 0° to 30°, preferably, from 6° to 9°, as illustrated in FIG. 2. Therefore, the latter forward helix track 106 and the former backward track have a natural transition which avoids backtrack to the first journey when going to the next cycling journey.

The assembling process of the surgical stapling head assembly with a rotary cutter is as follows: the metal cylinder member 105 is injection molded and nested on the outer wall of the anti-expansion tube 104, the bearing structure 109 is injection molded and fixed inside the staple driver 102, the staple driver and staple pushers are made integrally, the staple driver 102 is disposed inside the casing 101, by guiding projections 115a disposed on the inner wall of the bottom of the annular cutter 103, the annular cutter 103 is inserted via the entrance of the forward helix track 106 of the metal cylinder member 105 so that the annular cutter 103 is rotatably engaged with the metal cylinder member 105, the annular cutter 103 is able to perform rotary movement by the guide from the helix track, then the annular cutter 103 is fixed with the bearing structure 109 and the staple holder is placed in the casing 101 so that the assembling of rotary cutter is completed.

The instrument is triggered when using, the annular cutter 103 is pushed by the staple driver 102 to go up along a helical path under the co-operating between the guiding projection 115a and the forward helix track 106; and then the guiding projection 115a retreats in way of straight line along the backward track of the metal cylinder member 105, thus, a back and forth journey is completed. Because the backward track comprises a section of straight line track 107 and a section of arc track 108, the latter forward helix track 106 and the former backward track are able to have a natural transition so that the annular cutter 103 will not backtrack to the last journey when going to the next cycling journey, and the regular forward path of the annular cutter 103 is ensured.

Second Embodiment

A surgical stapling head assembly with a rotary cutter as illustrated from FIGS. 1 to 5, of which the structure is similar to that in the first embodiment. The staple driver 102 is internal injection molded and fixed with the bearing structure 109, the bearing structure 109 comprises the bearing inner ring 110 and the bearing outer ring 111, the ball 112 is disposed between the bearing inner ring 110 and the bearing outer ring 111 as a transmission part. When the friction between the bearing inner ring 110 and the bearing outer ring 111 is not large, the bearing inner ring 110 is able to be connected with the bearing outer ring 111 by means of friction without the ball 112 or other transmission parts disposed between the bearing inner ring 110 and the bearing outer ring 111.

Figure 3:
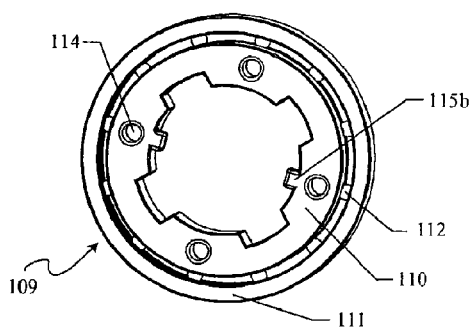
FIG. 3 is a schematic view of one bearing structure of the present invention.

As another configuration of the guiding structure, guiding projections 115b are disposed inside the bearing inner ring 110 as the guiding structure, as illustrated in FIG. 3, the guiding projection 115b engages with the track of the metal cylinder member 105 which is molded with the outside of the anti-expansion tube 104. When assembling, the guiding projection 115b of the bearing structure 109 is inserted via the entrance of the forward helix track 106 of the metal cylinder member 105 so that the staple driver 102 is disposed inside the casing 101, the annular cutter 103 is placed in the casing 101, the annular cutter 103 is fixed with the bearing inner ring 110 of the bearing structure 109 as illustrated in FIG. 4.

When the rotary cutter is assembled and connected with other parts of the surgical stapling head assembly, the instrument preparation work before surgery operation is done. In consideration of the whole surgical stapling head assembly, the working process of the rotary cutter during surgery operation is as follows: the surgery operator binds up the patient body tissues, and then the stapling instrument is adjusted to the most suitable distance for stapling, the trigger is tightly held for implementing triggering, the force is transformed by the transmission part inside the instrument to the push force that pushing the staple driver 102 to move forward, staples in the staple holder are pushed by the staple pushers arranged on the staple driver 102 into the tissues and shaped; at the same time, the guiding projection 115b goes forward along the forward helix track 106 of the metal cylinder member 105 so as to enable the annular cutter 103 to rotatably cut the tissues and the unwanted tissues will be cut by the cutting face of the cutter. When the triggering is finished, the guiding projection 115b goes to the backward track by the restoring and pulling force of the staple driver 102, the annular cutter 103 retreats to the inner cavity of the staple holder under the guide from the guiding projection 115b, thus one cutting journey is completed. Because the staple driver 102 is connected with the annular cutter 103 by the bearing structure 19, by use of the ball 112, the annular cutter 103 will not be subject to much friction when rotating. Furthermore, during the whole process of cutting, the annular cutter 103 is tightly connected with the staple driver 102, therefore, the annular cutter 103 will not shake or deviate from the central axis, the tissues will be cut in shape of a full circle, which avoids the potential danger of the cutter being stuck and unmovable.

On the other hand, by employing the surgical stapling head assembly with a rotary cutter of the present invention, the annular cutter 103 and the staple driver 102 go forward along the forward helix track 106 of the metal cylinder member 105, and retreat under the guide from the backward track, thereby the previous single track is divided into two, that is, the helix forward track 106 and the backward track, the helix forward track 106 and the backward track are independent but communicated to form a back and forth journey, the length of the whole metal cylinder member 105 at least comprises one back and forth journey. Furthermore, the backward track can be disposed into two sections, that is, a section of straight line track 107 and a section of arc track 108, as illustrated in FIG. 2, by disposing the arc track 108, the next forward helix track 106 will have a natural transition with the last backward track, which avoids backtrack of the annular cutter 103 to the first journey when going to the next cycling journey, the regular forward path of the annular cutter 103 is ensured, thereby the instrument can be operated more safely and reliable.

Third Embodiment

A surgical stapling head assembly with a rotary cutter as illustrated from FIGS. 1 to 9, of which the structure is similar to that in the first embodiment and second embodiment, the differences are that: the metal cylinder member 105 configured as illustrated in FIG. 2 is molded on the inner wall of the casing 101 (not shown in figures), guiding projections 115c are disposed on the bearing outer ring 111 or the outside of the bearing inner ring 110, as illustrated in FIGS. 6 and 7, alternatively, guiding projections 115c are disposed on the outside of the annular cutter 103 (not shown in figures), the guiding projections are set to engage with the helix forward track and backward track of the metal cylinder member 105.

For sake of easy combining and connecting, rivet holes 114 are disposed on said bearing inner ring 110 and connecting holes are disposed on the annular cutter 103 so that the bearing inner ring 110 and the annular cutter 103 can be fixed through rivets thereof. Of course, the involved connection can be by way of helix, shaping, pin, bonding, welding or clamping, etc. If the bearing structure 109 employs the similar structure of FIG. 8 or FIG. 9, the bearing outer ring 111 is in a structure of half enclosed, then rivet holes 114 can be disposed on the bearing outer ring 111.

When processing and assembling, the bearing structure 109 is fixedly connected with the annular cutter 103 as an assembled component at first, the connection can be by way of rivet, bonding or helix, etc. Then the assembled component is injection molded inside the staple driver 102 so as to make the bearing outer ring 111 to be integrally connected with the staple driver 102, the washer 113 can be disposed between the bearing structure 109 and the staple driver 102 when molding. In order to adapt to commonly used manufacture technique, the bearing outer ring 111 and the staple driver 102 can alternatively be connected in way of bonding or helix. When the above-mentioned works are finished, the assembly including the staple driver 102, the bearing structure 109 and the annular cutter 103 can be placed and mounted inside the casing 101, along the helix track by inserting the guiding projection 115c at the helix track entrance of the metal cylinder member 105 of the casing 101. When the assembling is done, the operation process is similar to that in the first embodiment and the second embodiment.

What is claimed is:

1. A surgical stapling head assembly with a rotary cutter, comprising a casing, an annular cutter, a staple driver and a staple holder, the casing is a tubular body comprising a stepped inner cavity and an anti-expansion tube, a plurality of staple pushers are arranged annularly and alternately in two rows, the staple driver is disposed between the anti-expansion tube and an inner wall of the casing, the staple driver is disposed at a proximal end of said staple pushers, the staple holder for receiving one or more surgical staples is disposed at a distal end of the staple driver, the annular cutter is disposed in the space formed by an inner wall of the staple holder, wherein said annular cutter is connected with the staple driver by a bearing structure, the bearing structure at least comprises a bearing inner ring and a bearing outer ring, guiding projections are disposed on said annular cutter or the bearing inner ring or the bearing outer ring, a metal cylinder member with guiding tracks is disposed inside the casing, said guiding projections engage with the guiding tracks so as to guide the annular cutter to move along a helical path.

2. The surgical stapling head assembly of claim 1, wherein said metal cylinder member is molded on an outer wall of the anti-expansion tube.

3. The surgical stapling head assembly of claim 1, wherein said metal cylinder member is molded on the inner wall of the casing.

4. The surgical stapling head assembly of any one of claims 1-3, wherein said guiding track comprises a helix forward track and a backward track, the helix forward track and the backward track are independent from each other but communicated with each other to form at least one back and forth journey.

5. The surgical stapling head assembly of claim 4, wherein said backward track comprises a section of straight line track and a section of arc track.

6. The surgical stapling head assembly of claim 5, wherein the angle between the two edges of the straight line track and the axis of the metal cylinder member is from 0° to 30°.

7. The surgical stapling head assembly of claim 1, wherein said bearing structure comprises the bearing inner ring, the bearing outer ring and a transmission part, the bearing inner ring is connected with the bearing outer ring by the transmission part, the annular cutter is fixed on the bearing inner ring or the bearing outer ring.

8. The surgical stapling head assembly of claim 7, wherein said bearing inner ring and said annular cutter can be fixed by rivets through the rivets holes thereof.

9. The surgical stapling head assembly of claim 7, wherein said bearing outer ring and the annular cutter can be fixed by rivets through the rivets holes thereof.

* * * * *